US 11,198,676 B2

(12) United States Patent
Kanbara et al.

(10) Patent No.: US 11,198,676 B2
(45) Date of Patent: Dec. 14, 2021

(54) PHENYL IMIDAZOLINE COMPOUND HAVING AMINOMETHYL GROUP OR SALT THEREOF, OR PHENYL TETRAHYDROPYRIMIDINE COMPOUND HAVING AMINOMETHYL GROUP OR SALT THEREOF, AND PRODUCTION METHOD FOR SUCH COMPOUNDS OR SALTS THEREOF

(71) Applicant: Mitsubishi Gas Chemical Company, Inc., Chiyoda-ku (JP)

(72) Inventors: Yutaka Kanbara, Niigata (JP); Emi Nakano, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 24 days.

(21) Appl. No.: 16/498,129

(22) PCT Filed: Mar. 23, 2018

(86) PCT No.: PCT/JP2018/011728
§ 371 (c)(1),
(2) Date: Sep. 26, 2019

(87) PCT Pub. No.: WO2018/181001
PCT Pub. Date: Oct. 4, 2018

(65) Prior Publication Data
US 2020/0339516 A1 Oct. 29, 2020

(30) Foreign Application Priority Data
Mar. 31, 2017 (JP) .............................. JP2017-071059

(51) Int. Cl.
*C08G 59/50* (2006.01)
*C07D 233/24* (2006.01)
*C07D 239/06* (2006.01)

(52) U.S. Cl.
CPC ......... *C07D 233/24* (2013.01); *C07D 239/06* (2013.01); *C08G 59/5073* (2013.01)

(58) Field of Classification Search
CPC ....................... C07D 233/24; C08G 59/5073
USPC ....................................................... 523/461
See application file for complete search history.

(56) References Cited

U.S. PATENT DOCUMENTS 2,505,247 A * 4/1950 Isler ..................... C07D 233/06
548/355.1
4,816,589 A * 3/1989 Lin ....................... C07D 231/12
548/335.5

2011/0201589 A1 8/2011 Madden et al.
2014/0073627 A1 3/2014 Madden et al.
2016/0176827 A1 6/2016 Kanbara et al.

FOREIGN PATENT DOCUMENTS

| DE | 40 24 259 A1 | 2/1992 |
| EP | 2 592 099 A1 | 5/2013 |
| EP | 3 031 803 A1 | 6/2016 |
| JP | 7-10871 A | 1/1995 |
| JP | 10-45736 A | 2/1998 |
| JP | 2012-500783 A | 1/2012 |
| WO | WO 2010/020556 A1 | 2/2010 |
| WO | WO 2015/019777 A1 | 2/2015 |

OTHER PUBLICATIONS

International Search Report dated May 1, 2018 in PCT/JP2018/011728 filed on Mar. 23, 2018.
Database Registry, Nov. 2016, RN 2022733-34-0, RN 1872798-00-9, RN 1856802-34-0, Retrieved from STN international [online]; retrieved on Apr. 12, 2018, 2 total pages.
The 4th series of Experimental Chemistry, "Organic Synthesis II—Alcohols and Amines-", The Chemical Society of Japan, vol. 20, 1992, pp. 279-282, 4 total pages.
Review of Epoxy Resin, Basics Edition I, The Japan Society of Epoxy Resin Technology, 2003, pp. 123-125 and 148, 4 total pages.
An, S. et al., "Microwave-Assisted Cascade Cycloaddition for C—N Bond Formation: An Approach to the Construction of 1,4,5,6-Tetrahydropyrimidine and 2-Imidazoline Derivatives," Synthesis, vol. 45, 2013, pp. 2525-2532.

* cited by examiner

*Primary Examiner* — Michael J Feely
(74) *Attorney, Agent, or Firm* — Oblon, McClelland, Maier & Neustadt, L.L.P.

(57) ABSTRACT

In order to provide a novel phenyl imidazoline compound having an aminomethyl group, a novel phenyl tetrahydropyrimidine compound having an aminomethyl group, or the like, a compound according to the present invention or a salt thereof is represented by the following formula (1):

$$H_2NH_2C-\text{[phenyl]}(R_1)-\text{[imidazoline/tetrahydropyrimidine ring with HN, N, R}_2\text{]}_n \quad (1)$$

wherein $R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 or 2.

6 Claims, 12 Drawing Sheets

PHENYL IMIDAZOLINE COMPOUND HAVING AMINOMETHYL GROUP OR SALT THEREOF, OR PHENYL TETRAHYDROPYRIMIDINE COMPOUND HAVING AMINOMETHYL GROUP OR SALT THEREOF, AND PRODUCTION METHOD FOR SUCH COMPOUNDS OR SALTS THEREOF

TECHNICAL FIELD

The present invention relates to a phenyl imidazoline compound having an aminomethyl group or a salt thereof, or a phenyl tetrahydropyrimidine compound having an aminomethyl group or a salt thereof, and a production method for such compounds or salts thereof.

BACKGROUND ART

Phenyl imidazoline compounds and phenyl tetrahydropyrimidine compounds are useful compounds as building blocks for medicinal products since they are biologically and/or pharmacologically active. In addition, these compounds are useful as raw materials or additives for polymers. Phenyl imidazoline is a known curing agent and/or curing accelerator for epoxy resins and it is one of the important compounds serving as raw materials for compositions. As examples of such compounds, Patent Document 1 describes a diamino-s-triazine compound having an imidazoline ring, and Non-Patent Document 1 describes 2-phenylimidazole having an imidazoline ring. Non-Patent Document 2 describes methods for producing cyanophenyl imidazoline and cyanophenyl tetrapyrimidine. In the meantime, meta-xylenediamine (MXDA)—an example aminomethyl benzene compound having an aminomethyl group—is used as a raw material for polyamides and polyurethanes, and, in particular, it is widely known as an epoxy resin curing agent. Such meta-xylenediamine is also one of the important compounds serving as a raw material for compositions. Non-Patent Document 1 describes such aminomethyl group-containing meta-xylenediamine as an epoxy resin curing agent.

CITATION LIST

Patent Document

Patent Document 1: JPH07-010871 A

Non-Patent Document

Non-Patent Document 1: Review of Epoxy Resins, Basics I, p.p. 123-125 and 148, The Japan Society of Epoxy Resin Technology Non-Patent Document 2: SYNTHESIS, Vol. 45, p.p. 2525-2532, 2013

SUMMARY

However, a phenyl imidazoline compound having an aminomethyl group or a salt thereof, and a phenyl tetrahydropyrimidine compound having an aminomethyl group or a salt thereof, are not known. These compounds or salts thereof are expected to be an important compound in synthetic organic chemistry that can be used as raw materials for polymers and pharmaceutical intermediates, and particularly as curing agents for epoxy resins.

Under the above circumstances, an object of the present invention is to provide a novel phenyl imidazoline compound having an aminomethyl group or a salt thereof, or a novel phenyl tetrahydropyrimidine compound having an aminomethyl group or a salt thereof, and to provide an industrially advantageous method for producing such compounds or salts thereof.

As a result of intensive studies, the present inventors have found that a phenyl imidazoline compound having an aminomethyl group or a salt thereof, or a phenyl tetrahydropyrimidine compound having an aminomethyl group or a salt thereof, can be produced through reaction of a cyanobenzylamine compound or a salt thereof with an ethylenediamine compound or a salt thereof or with a propanediamine compound or a salt thereof, or can be produced through hydrogen reduction of a cyanophenyl imidazoline compound or a salt thereof or hydrogen reduction of a cyanophenyl tetrahydropyrimidine compound or a salt thereof. With this finding, the present inventors have completed the present invention.

Specifically, the present invention is as follows:

[1]

A compound represented by formula (1) below, or a salt thereof:

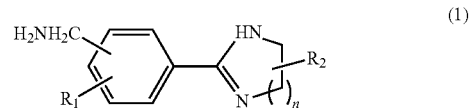

wherein $R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 or 2.

[2]

The compound as defined in [1] or a salt thereof, wherein the compound represented by formula (1) or a salt thereof is p-aminomethyl phenyl imidazoline represented by formula (2) below or a salt thereof; m-aminomethyl phenyl tetrahydropyrimidine represented by formula (3) below or a salt thereof; m-aminomethyl phenyl imidazoline represented by formula (4) below or a salt thereof; or 3-methyl-4-aminomethyl phenyl imidazoline represented by formula (5) below or a salt thereof:

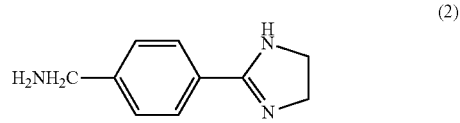

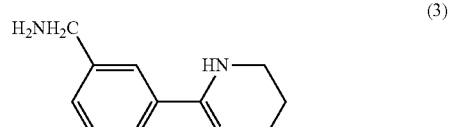

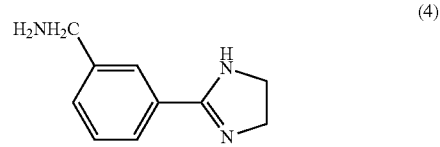

-continued

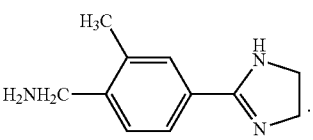
(5)

[3]
A method for producing a compound represented by formula (1) below or a salt thereof, the method comprising a reaction step of reacting a cyanobenzylamine compound represented by formula (6) below or a salt thereof with an ethylenediamine compound represented by formula (7) below or a salt thereof, or with a propanediamine compound represented by formula (7) below or a salt thereof, to obtain a compound represented by formula (1) below or a salt thereof:

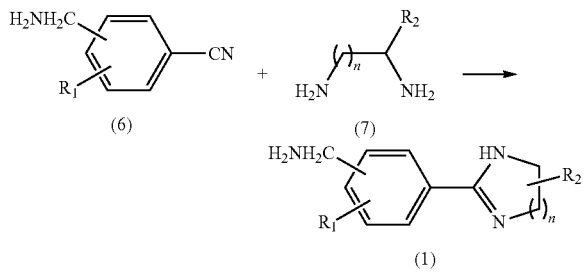

wherein, in formula (1), formula (6) and formula (7), $R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 or 2.

[4]
A method for producing a compound represented by formula (1) below or a salt thereof, the method comprising a reduction step of reducing, with hydrogen, a cyanophenyl imidazoline compound represented by formula (8) below or a salt thereof, or a cyanophenyl tetrahydropyrimidine compound represented by formula (8) below or a salt thereof, in the presence of a catalyst and a solvent, to obtain a compound represented by formula (1) below or a salt thereof:

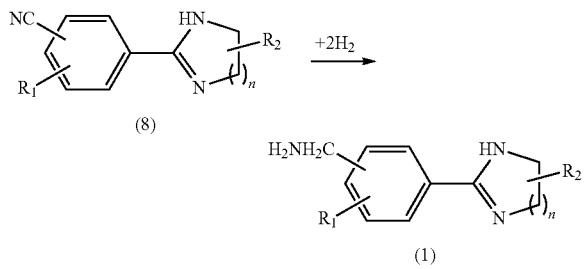

wherein, in formula (1) and formula (8), $R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 or 2.

[5]
An epoxy resin curing agent comprising a compound as defined in [1] or [2], or a salt thereof.

[6]
An epoxy resin composition comprising:
an epoxy resin; and
an epoxy resin curing agent as defined in [5].

Advantageous Effects of Invention

The present invention can provide a novel phenyl imidazoline compounds having an aminomethyl group or a salt thereof, or a novel phenyl tetrahydropyrimidine compound or a salt thereof, and can also provide an industrially advantageous method for producing such compounds or salts thereof.

DESCRIPTION OF EMBODIMENTS

Figure 1:
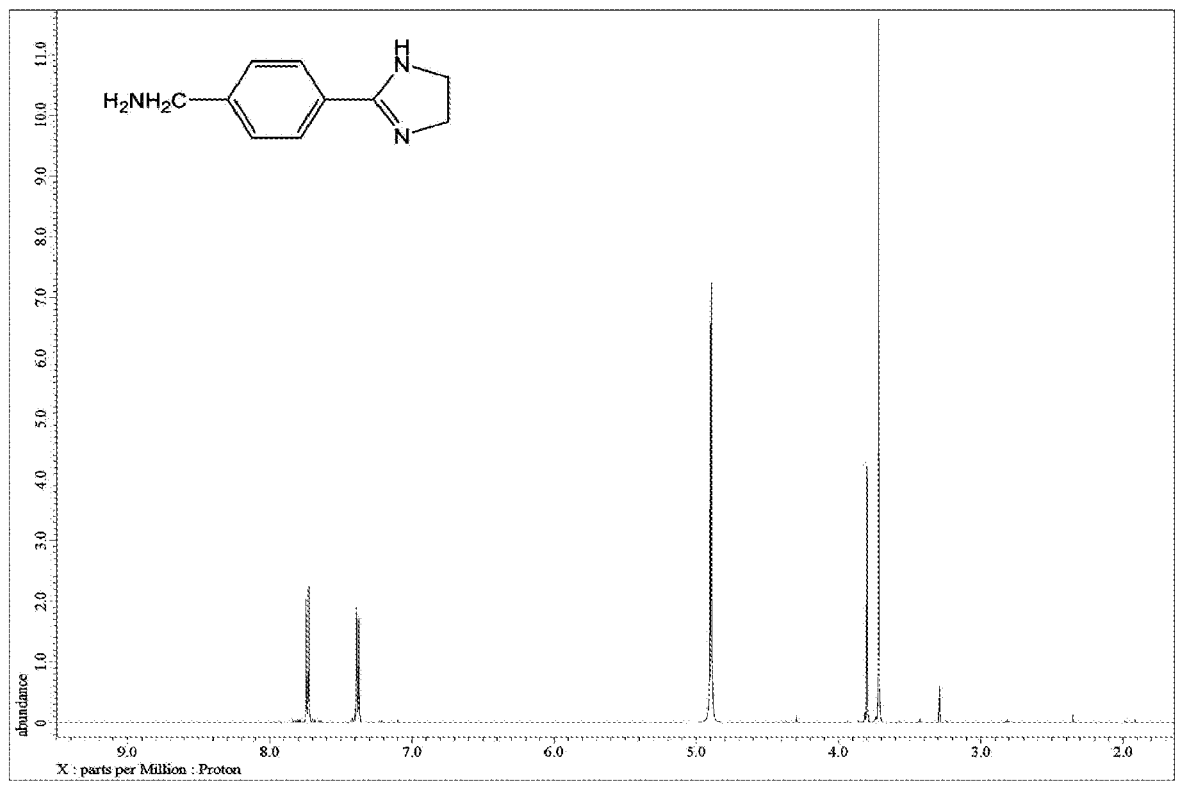
FIG. 1 is a $^1$H-NMR chart of p-aminomethyl phenyl imidazoline.

Hereinafter, an embodiment of the present invention (hereinafter referred to as the "present embodiment") will be described in detail. However, the present invention is not limited to the below embodiment and can be modified in various ways without departing from the gist of the present invention.

[Phenyl Imidazoline Compound Having an Aminomethyl Group or a Salt Thereof, or Phenyl Tetrahydropyrimidine Compound Having an Aminomethyl Group or a Salt Thereof]

A phenyl imidazoline compound or phenyl tetrahydropyrimidine compound having an aminomethyl group according to the present embodiment is represented by the following formula (1):

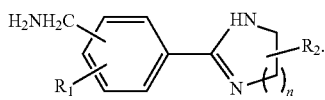
(1)

In formula (1), $R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 or 2.

In formula (1), examples of the alkyl group having 1 to 10 carbon atoms represented by $R_1$ and $R_2$ may include, but are not particularly limited to, a methyl group, an ethyl group, a linear or branched propyl group, a linear or branched butyl group, a linear or branched pentyl group, a linear or branched hexyl group, a linear or branched heptyl group, a linear or branched octyl group, a linear or branched nonyl group, a linear or branched decyl group, and a cyclic cyclohexyl group.

In formula (1), examples of the alkoxy group having 1 to 10 carbon atoms represented by $R_1$ and $R_2$ may include, but are not particularly limited to, a methoxy group, an ethoxy group, a linear or branched propoxy group, a linear or branched butoxy group, and a cyclic cyclohexyloxy group.

In formula (1), examples of the aryl group having 6 to 10 carbon atoms represented by $R_1$ and $R_2$ may include, but are not particularly limited to, a phenyl group and a benzyl group.

In formula (1), examples of the aryloxy group having 6 to 10 carbon atoms represented by $R_1$ and $R_2$ may include, but are not particularly limited to, a phenoxy group.

In formula (1), examples of the halogen atom represented by $R_1$ and $R_2$ may include a chlorine atom, a fluorine atom, and a bromine atom.

The compound represented by formula (1) according to the present embodiment is not particularly limited, and examples thereof may include p-aminomethyl phenyl imidazoline represented by formula (2) below, m-aminomethyl phenyl tetrahydropyrimidine represented by formula (3) below, m-aminomethyl phenyl imidazoline represented by formula (4) below, and 3-methyl-4-aminomethyl phenyl imidazoline represented by formula (5) below:

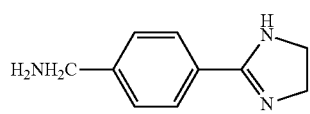
(2)

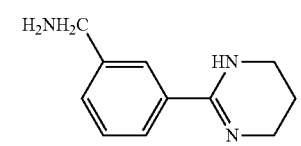
(3)

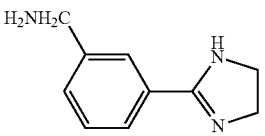
(4)

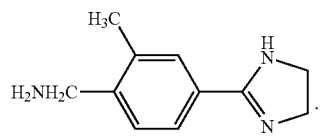
(5)

A salt of the compound represented by formula (1) above is not particularly limited, and examples thereof may include salts obtained from the compound represented by formula (1) and an inorganic acid and/or an organic acid. In particular, salts obtained from the compound represented by formula (1) and any of hydrochloric acid, carbonic acid or acetic acid are preferable.

[Production Method for a Phenyl Imidazoline Compound Having an Aminomethyl Group or a Salt Thereof, or a Phenyl Tetrahydropyrimidine Compound Having an Aminomethyl Group or a Salt Thereof]

In the present embodiment, the compound represented by the above-mentioned formula (1) or a salt thereof can be produced by a method including a reaction step of reacting a cyanobenzylamine compound represented by formula (6) below or a salt thereof with an ethylenediamine compound represented by formula (7) below or a salt thereof, or with a propanediamine compound represented by formula (7) below or a salt thereof, to thereby obtain the compound represented by formula (1) or a salt thereof (this method will be referred to as "production method 1"), or a method including a reduction step of reducing, with hydrogen, a cyanophenyl imidazoline compound represented by formula (8) below or a salt thereof, or a cyanophenyl tetrahydropyrimidine compound represented by formula (8) below or a salt thereof, which will be described below, in the presence of a catalyst and a solvent, to thereby obtain the compound represented by formula (1) or a salt thereof (this method will be referred to as "production method 2").

[Production Method 1]

[Reaction Step]

The reaction step is a step of reacting a cyanobenzylamine compound represented by formula (6) below or a salt thereof with an ethylenediamine compound represented by formula (7) below or a salt thereof, or with a propanediamine compound represented by formula (7) below or a salt thereof, to thereby obtain the compound represented by formula (1) below or a salt thereof. The reaction of a cyanobenzylamine compound or a salt thereof with an ethylenediamine compound or a salt thereof or with a propanediamine compound or a salt thereof is represented by the following reaction formula:

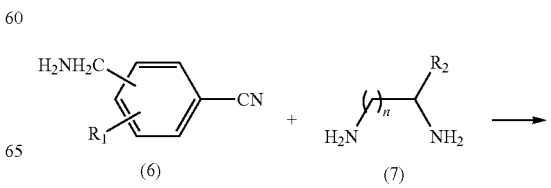

-continued

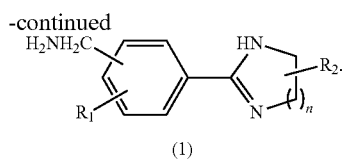

(1)

In formula (1), formula (6) and formula (7), $R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 or 2.

(Cyanobenzylamine Compound or a Salt Thereof)

In formula (6), examples of the alkyl group having 1 to 10 carbon atoms represented by $R_1$ and $R_2$ may include a methyl group, an ethyl group, a linear or branched propyl group, a linear or branched butyl group, a linear or branched pentyl group, a linear or branched hexyl group, a linear or branched heptyl group, a linear or branched octyl group, a linear or branched nonyl group, a linear or branched decyl group, and a cyclic cyclohexyl group.

In formula (6), examples of the alkoxy group having 1 to 10 carbon atoms represented by $R_1$ and $R_2$ may include a methoxy group, an ethoxy group, a linear or branched propoxy group, a linear or branched butoxy group, and a cyclic cyclohexyloxy group.

In formula (6), examples of the aryl group having 6 to 10 carbon atoms represented by $R_1$ and $R_2$ may include, but are not particularly limited to, a phenyl group and a benzyl group.

In formula (6), examples of the aryloxy group having 6 to 10 carbon atoms represented by $R_1$ and $R_2$ may include, but are not particularly limited to, a phenoxy group.

In formula (6), examples of the halogen atom represented by $R_1$ and $R_2$ may include a chlorine atom, a fluorine atom, and a bromine atom. Further, a salt obtained by neutralizing the amino group of a cyanobenzylamine compound or a salt thereof with an acid, such as hydrochloric acid, may also be used in the reaction step.

Examples of the cyanobenzylamine compound represented by formula (6) may include, but are not particularly limited to, o-cyanobenzylamine, m-cyanobenzylamine, p-cyanobenzylamine, 3,5-bis(aminomethyl)benzonitrile, 2,5-bis(aminomethyl)benzonitrile and 2,4-bis(aminomethyl)benzonitrile.

A salt of the cyanobenzylamine compound represented by formula (6) is not particularly limited, and examples thereof may include salts obtained from the cyanobenzylamine compound and an inorganic acid and/or an organic acid. In particular, salts obtained from the cyanobenzylamine compound and any of hydrochloric acid, carbonic acid and acetic acid are preferable.

(Ethylenediamine Compound or a Salt Thereof, or Propanediamine Compound or a Salt Thereof)

In the ethylenediamine compound or propanediamine compound represented by the above formula (7), a carbon atom may be with or without a substituent. Examples of the compound where n is 1 (n=1) may include ethylenediamine, 1,2-propanediamine, 1,2-butanediamine, 3,4-butanediamine, and salts thereof, and ethylenediamine is preferable among these. Examples of the compound where n is 2 (n=2) may include 1,3-propanediamine, 1,3-butanediamine, 1,3-pentanediamine, 2,4-pentanediamine, and salts thereof, and 1,3-propanediamine is preferable among these.

A salt of the ethylenediamine compound or propanediamine compound represented by formula (7) is not particularly limited, and examples thereof include salts with an inorganic acid and/or an organic acid. In particular, salts with any of hydrochloric acid, carbonic acid and acetic acid are preferable.

The amount of the ethylenediamine compound or propanediamine compound represented by formula (7) or a salt thereof used may be selected as appropriate, depending on the reaction conditions. Such amount is preferably 0.05 to 50 moles, more preferably 0.1 to 10 moles, and still more preferably 0.2 to 5 moles, per mole of the cyanobenzylamine compound represented by formula (6) or a salt thereof.

(Catalyst)

A catalyst may be used in the reaction of the cyanobenzylamine compound or a salt thereof with the ethylenediamine compound or a salt thereof, or with the propanediamine compound or a salt thereof. Examples of such catalyst used may include, but are not particularly limited to, elemental sulfur and sulfur compounds, as well as metallic compounds, such as compounds of copper, zinc, iron, cobalt, manganese, aluminum, tin, mercury, chromium, and cadmium. Among these, copper, zinc or cobalt compounds are suitably used.

Such copper, zinc or cobalt compounds are not particularly limited, and examples thereof may include hydroxides, fluorides, chlorides, bromides, iodides, oxides, sulfides, carbonates, hydrogencarbonates, sulfates, nitrates, and salts of organic acid, such as formic acid, acetic acid or propionic acid. Among these, copper acetate is preferable, as it is inexpensive and readily available.

The amount of the catalyst used is not particularly limited, and it is preferably 0.00010 to 100 parts by mass, more preferably 0.0010 to 10 parts by mass, and still more preferably 0.0050 to 50 parts by mass, based on one (1) part by mass of the cyanobenzylamine compound or a salt thereof. The reaction tends to proceed more efficiently when the amount of the catalyst used is 0.00010 parts by mass or more. The reaction tends to be more economically advantageous when the amount of the catalyst used is 100 parts by mass or less.

(Solvent)

A solvent may be used in the reaction of the cyanobenzylamine compound or a salt thereof with the ethylenediamine compound or a salt thereof, or with the propanediamine compound or a salt thereof. Examples of such solvent used may include, but are not particularly limited to: water; alcohols, such as methanol, ethanol, propanol, and butanol; hydrocarbons, such as hexane, benzene, toluene, and xylene; ethers, such as tetrahydrofuran; amides, such as dimethylformamide; and amines, such as benzylamine and xylenediamine. Two or more of these may be used in combination. Among these, xylenes are preferable as they are suited for separation of ammonia and have high reflux temperature.

The amount of solvent used is not particularly limited, and it is preferably 0.010 to 1,000 parts by mass, more preferably 0.1 to 100 parts by mass, and still more preferably 1.0 to 50 parts by mass, based on the total amount of the raw material cyanobenzylamine compound or a salt thereof and the raw material ethylenediamine compound or propanediamine compound or a salt thereof. The reaction tends to proceed more efficiently when the amount of the solvent used is 0.010 parts by mass or more. The reaction tends to be more economically advantageous when the amount of the solvent used is 1,000 parts by mass or less.

An atmosphere of the reaction is not particularly limited. For example, a nitrogen atmosphere and a noble-gas atmosphere which are stable in the reaction system may be employed.

For the reaction system, a given system, such as a batch system or a continuous flow system, may be selected. When a batch system is selected, a given order of adding raw materials may be selected.

The compound represented by formula (1) above or a salt thereof can be easily recovered from the reaction solution using a routine method, e.g., distillation, recrystallization, extraction, etc. Among these, separation by distillation is a simple method and is therefore particularly preferable.

The reaction pressure is not particularly limited, and the reaction may be suitably performed under a reflux condition at reduced pressure or atmospheric pressure, or in a sealed vessel under the pressure of the solvent itself.

The reaction temperature may be adjusted as appropriate according to the raw material feed ratio and the conditions of the reaction. The reaction temperature is preferably 20 to 300° C., more preferably 50 to 250° C., and still more preferably 70 to 200° C.

The reaction time may be adjusted as appropriate according to the raw material feed ratio and the conditions of the reaction. In the case of a batch system, the reaction time is preferably 1 minute to 100 hours, more preferably 5 minutes to 50 hours, and still more preferably 10 minutes to 10 hours.

[Production Method 2]
[Reduction Step]

The reduction step is a step of reducing, with hydrogen, a cyanophenyl imidazoline compound represented by formula (8) below or a salt thereof, or a cyanophenyl tetrahydropyrimidine compound represented by formula (8) below or a salt thereof, in the presence of a catalyst and a solvent, to thereby obtain the phenyl imidazoline compound having an aminomethyl group represented by formula (1) below or a salt thereof, or the phenyl tetrahydropyrimidine compound having an aminomethyl group represented by formula (1) below or a salt thereof.

The hydrogen reduction reaction of the cyanophenyl imidazoline compound or a salt thereof or the hydrogen reduction reaction of the cyanophenyl tetrahydropyrimidine compound or a salt thereof is as described below. The method of hydrogen reduction is not particularly limited. For example, hydrogen reduction may be carried out by feeding the raw material (i.e., a cyanophenyl imidazoline compound or a salt thereof, or a cyanophenyl tetrahydropyrimidine compound or a salt thereof) into the reaction vessel together with the catalyst, solvent and hydrogen, in order to cause the reaction.

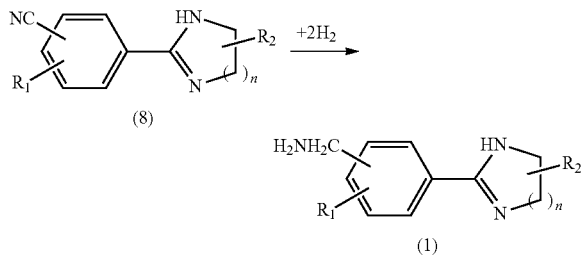

In the above formula (1) and formula (8), $R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 or 2.

(Cyanophenyl Imidazoline Compound or a Salt Thereof, or Cyanophenyl Tetrahydropyrimidine Compound or a Salt Thereof)

In formula (8), examples of the alkyl group having 1 to 10 carbon atoms represented by $R_1$ and $R_2$ may include a methyl group, an ethyl group, a linear or branched propyl group, a linear or branched butyl group, a linear or branched pentyl group, a linear or branched hexyl group, a linear or branched heptyl group, a linear or branched octyl group, a linear or branched nonyl group, a linear or branched decyl group, and a cyclic cyclohexyl group.

In formula (8), examples of the alkoxy group having 1 to 10 carbon atoms represented by $R_1$ and $R_2$ may include a methoxy group, an ethoxy group, a linear or branched propoxy group, a linear or branched butoxy group, and a cyclic cyclohexyloxy group.

In formula (8), examples of the aryl group having 6 to 10 carbon atoms represented by $R_1$ and $R_2$ may include, but are not particularly limited to, a phenyl group and a benzyl group.

In formula (8), examples of the aryloxy group having 6 to 10 carbon atoms represented by $R_1$ and $R_2$ may include, but are not particularly limited to, a phenoxy group.

In formula (8), examples of the halogen atom represented by $R_1$ and $R_2$ include a chlorine atom, a fluorine atom, and a bromine atom.

Examples of the cyanophenyl imidazoline compound or cyanophenyl tetrahydropyrimidine compound represented by formula (8) above may include, but are not particularly limited to, o-cyanophenyl imidazoline, m-cyanophenyl imidazoline, p-cyanophenyl imidazoline, o-cyanophenyl tetrahydropyrimidine, m-cyanophenyl tetrahydropyrimidine, and p-cyanophenyl tetrahydropyrimidine compounds.

A salt of the cyanophenyl imidazoline compound or cyanophenyl tetrahydropyrimidine compound represented by the above formula (8) is not particularly limited, and examples may include salts obtained from the cyanophenyl imidazoline compound or cyanophenyl tetrahydropyrimidine compound with an inorganic acid and/or an organic acid. In particular, salts obtained from the cyanophenyl imidazoline compound or cyanophenyl tetrahydropyrimidine compound with any of hydrochloric acid, carbonic acid and acetic acid are preferable examples.

(Catalyst)

In the hydrogen reduction, any catalyst having hydrogen reduction activity can be used without limitation, and examples of such catalyst may include: catalysts of noble metals, such as nickel, cobalt, palladium and platinum, affixed to a support, such as silica, alumina, zirconia, titania and magnesia, at a high dispersion rate; and sponge metal catalysts obtained by developing nickel-aluminum or cobalt-aluminum alloys with an alkali. Among these, nickel sponge metal catalysts are relatively inexpensive and have relatively high activity, and are therefore preferably used. These catalysts may be used alone or in a combination of two or more.

These catalysts may be in a powdery or granular form and used in a slurry bed reactor. Alternatively, such catalysts may be in pellets or pulverized and used in a fixed bed reactor.

The amount of the catalyst used is not particularly limited and it is preferably 0.00010 to 1,000 parts by mass, more preferably 0.0010 to 10 parts by mass, and still more preferably 0.010 to 1.0 parts by mass, based on one (1) part by mass of the cyanophenyl imidazoline compound or cyanophenyl tetrahydropyrimidine compound, or a salt thereof. The reaction tends to proceed more efficiently when the amount of the catalyst used is 0.00010 parts by mass or more. The reaction tends to be more economically advantageous when the amount of the catalyst used is 1,000 parts by mass or less.

(Solvent)

The solvent used in the hydrogen reduction is not particularly limited and examples thereof may include: water; alcohols, such as methanol, ethanol, and propanol; hydrocarbons, such as hexane, benzene, toluene, and xylene; ethers, such as tetrahydrofuran; amides, such as dimethylformamide; ammonia and the like; and amines, such as benzylamine and xylenediamine. Among these, methyl cellosolve (2-methoxyethanol) is particularly preferable as it provides high solubility for the raw materials and the resulting product. The solvents may be used alone, or in a combination of two or more.

The amount of the solvent used is not particularly limited, and it is preferably 0.10 to 1,000 parts by mass, more preferably 1.0 to 100 parts by mass, and still more preferably 5.0 to 50 parts by mass, based on one (1) part by mass of the cyanophenyl imidazoline compound or cyanophenyl tetrahydropyrimidine compound, or a salt thereof. When the amount of the solvent used is 0.10 parts by mass or more, the raw materials and the resulting product become more soluble, so that the reaction tends to proceed more efficiently. When the amount of the solvent used is 1,000 parts by mass or less, the reaction tends to be more economically advantageous.

A basic compound, such as an alkali metal compound, an alkaline earth metal compound, and an amine compound, may be added into the above-described solvents in order to increase the selectivity. Among such basic compounds, potassium hydroxide and sodium hydroxide are preferable in terms of the effect of such addition and economic efficiency. Such basic compounds may be used alone or in a combination of two or more.

The amount of the basic compound used is not particularly limited, and it is preferably 0.00010 to 100 parts by mass, more preferably 0.001 to 10 parts by mass, and still more preferably 0.0050 to 5 parts by mass, based on one (1) part by mass of the cyanophenyl imidazoline compound or cyanophenyl tetrahydropyrimidine compound, or a salt thereof. The reaction tends to proceed more efficiently when the amount of the basic compound used is 0.00010 parts by mass or more. The reaction tends to be more economically advantageous when the amount of the basic compound used is 100 parts by mass or less.

(Hydrogen)

The amount of hydrogen used for the hydrogen reduction is not particularly limited. Usually, hydrogen is used in large excess relative to the cyanophenyl imidazoline compound or cyanophenyl tetrahydropyrimidine compound, or a salt thereof. Hydrogen may be used after it is diluted with nitrogen, an inert gas, etc., which is stable under the reaction conditions.

For the reaction system, a given system, such as a batch system or a continuous flow system, may be selected. When a batch system is selected, any order of adding raw materials may be selected.

The phenyl imidazoline compound having an aminomethyl group, or a salt thereof, or the phenyl tetrahydropyrimidine compound having an aminomethyl group, or a salt thereof, can be easily recovered from the reaction solution using a routine method, e.g., distillation, recrystallization, extraction, etc.

The reaction pressure is not particularly limited and is preferably 0 to 100 MPa, more preferably 1 to 50 MPa, and still more preferably 2 to 10 MPa.

The reaction temperature may be adjusted as appropriate according to the raw material feed ratio and the conditions of the reaction. The reaction temperature is preferably 0 to 200° C., more preferably 10 to 150° C., and still more preferably 20 to 100° C.

The reaction time may be adjusted as appropriate according to the raw material feed ratio and the conditions of the reaction. In the case of a batch system, the reaction time is preferably 1 minute to 5,000 minutes, more preferably 5 minutes to 1,000 minutes, and still more preferably 10 minutes to 500 minutes.

[Use of a Phenyl Imidazoline Compound Having an Aminomethyl Group or a Salt Thereof, or a Phenyl Tetrahydropyrimidine Compound Having an Aminomethyl Group or a Salt Thereof]

The compound represented by the above-described formula (1) according to the present embodiment, or a salt thereof, can be used as a raw material for polymers and an intermediate for pharmaceuticals, and it is particularly useful as a curing agent for epoxy resins.

[Resin Composition]

The resin composition according to the present embodiment is an epoxy resin composition including: a thermosetting resin (in particular, an epoxy resin); and the above-described compound represented by formula (1) above according to the present embodiment, or a salt thereof, as a curing agent for the epoxy resin.

The content of the compound represented by formula (1) above according to the present embodiment, or a salt thereof, serving as an epoxy resin curing agent, in the resin composition of the present embodiment is not particularly limited. Preferably, the number of moles of hydrogen in the amino group which is contained in the compound represented by formula (1) above, or a salt thereof, and which is to be reacted with the epoxy group contained in the epoxy resin, is preferably at a molar ratio of 0.01 to 100 relative to one mole of the epoxy group in the epoxy resin. The above molar ratio is more preferably 0.05 to 50 and still more preferably 0.1 to 10. When the content falls within the range described above, the epoxy resin exhibits further improved curable properties, and the heat resistance of the resulting cured product can also be further improved. In addition, the drying properties of a coating of the resin composition can also be improved.

EXAMPLES

The present invention will now be described more specifically by using the Examples and Comparative Examples set forth below. However, the Examples below in no way limit the present invention.

The raw materials used were commercially available reagents (manufactured by Wako Pure Chemical Industries, Ltd., Tokyo Chemical Industry Co., Ltd., Sigma-Aldrich Co., LLC, and Ark Pharm, Inc.). Each component was identified from the spectra of NMR (with deuterated DMSO or deuterated methanol solvent), IR and GC-MS. Each reaction solution was analyzed by gas chromatography based on an internal standard method. It is to be noted that the value of the yield is represented in mole percent.

Synthesis Example 1 (Synthesis of 4-Cyanobenzylamine)

4-Cyanobenzylamine hydrochloride (12.8 g), purified water (73.1 g), and sodium hydroxide (3.1 g) were placed in a 200 mL conical flask, to cause precipitation of a solid. The solvent was extracted using ethyl acetate, and then removed using an evaporator, to thereby obtain 4-cyanobenzylamine at a yield of 74%.

Synthesis Example 2 (Synthesis of m-Cyanophenyl Imidazoline)

Isophthalonitrile (10.4 g), ethylenediamine (6.0 g), copper acetate (1.5 g) and meta-xylene (49.2 g) were fed into a 200 mL three-necked flask equipped with a thermometer sleeve and a reflux condenser, and heated for reflux at 134° C. for 9 hours while being stirred under atmospheric pressure. After that, the resulting mixture in the flask was left to cool, and filtered to obtain the precipitated crystal. The obtained crystal was washed with a small amount of meta-xylene, and then vacuum-dried, to thereby obtain m-cyanophenyl imidazoline at a yield of 60%.

Synthesis Example 3 (Synthesis of 3-Methyl-4-Cyanophenyl Imidazoline)

2-Methylterephthalonitrile (5.0 g), ethylenediamine (2.8 g), copper acetate (0.7 g) and meta-xylene (25.2 g) were fed into a 100 mL three-necked flask equipped with a thermometer sleeve and a reflux condenser, and heated for reflux at 134° C. for 19 hours while being stirred under atmospheric pressure. After that, the resulting mixture in the flask was left to cool to obtain a solid precipitate, which was then dissolved in tetrahydrofuran. The resulting solution was filtered to separate the catalyst. Further, the solvent was concentrated using an evaporator, followed by simple distillation using a Kugelrohr apparatus, to thereby obtain 3-methyl-4-cyanophenyl imidazoline at a yield of 76%.

Example 1 p-Aminomethyl Phenyl Imidazoline

Figure 2:
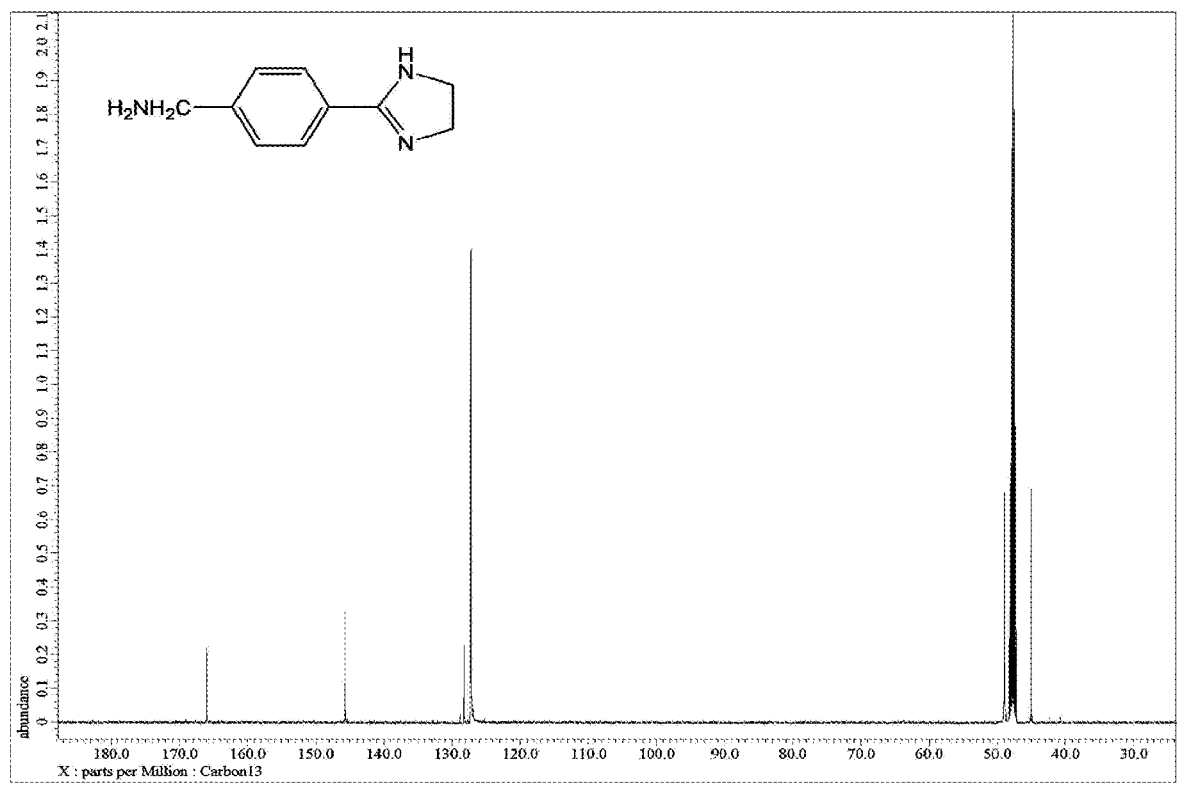
FIG. 2 is a $^{13}$C-NMR chart of p-aminomethyl phenyl imidazoline.
Figure 3:
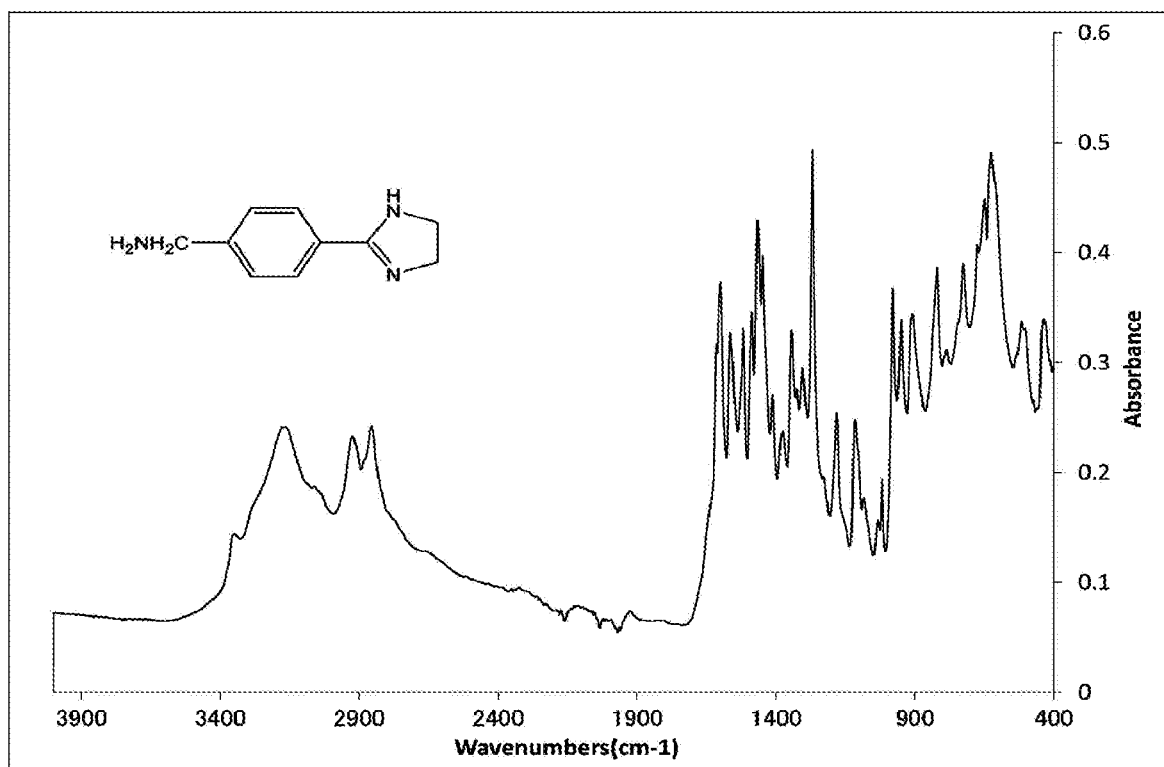
FIG. 3 is an IR chart of p-aminomethyl phenyl imidazoline.
Figure 4:
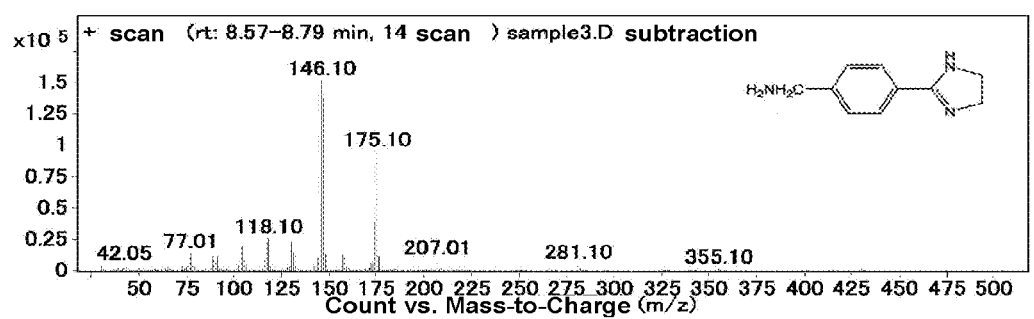
FIG. 4 is a GC-MS EI+ chart of p-aminomethyl phenyl imidazoline.

The 4-cyanobenzylamine (5.0 g) obtained in Synthesis Example 1, ethylenediamine (3.0 g), copper acetate (0.7 g) and meta-xylene (25.0 g) were fed into a 100 mL three-necked flask equipped with a thermometer sleeve and a reflux condenser, and heated for reflux at 134° C. for 5.7 hours while being stirred under atmospheric pressure. After that, the component of interest was extracted with ethyl acetate, and the solvent was concentrated using an evaporator, followed by simple distillation using a Kugelrohr apparatus, to thereby obtain 0.3 g of a yellow solid. This yellow solid was confirmed as being p-aminomethyl phenyl imidazoline based on the $^1$H- and $^{13}$C-NMR charts (FIGS. 1 and 2), the IR chart (FIG. 3) and the GC-MS El+ chart (FIG. 4). Further, the reaction solution after the separation of the catalyst and insoluble matter by filtration was analyzed by gas chromatography, to find that the yield of the p-aminomethyl phenyl imidazoline was 49%.

In the identification, the following peaks, etc., were found in the NMR and IR charts.

NMR (d4-Methanol): $^1$H δ 7.38-7.74, 4H (benzene ring), 3.8, 2H (—CH$_2$-Ph), 3.72, 4H (—CH$_2$—CH$_2$— of imidazoline ring), $^{13}$C δ 166 (C of imidazoline ring), 127-146 (benzene ring), 49.0 (—CH$_2$—CH$_2$— of imidazoline ring), 45.1 (NH$_2$—CH$_2$-Ph) ppm IR (ATR method): ν 3174, 2924, 2855, 1599, 1465, 1269, 979, 820, 625 cm$^{-1}$ Example 2 m-Aminomethyl Phenyl Tetrahydropyrimidine

Figure 5:
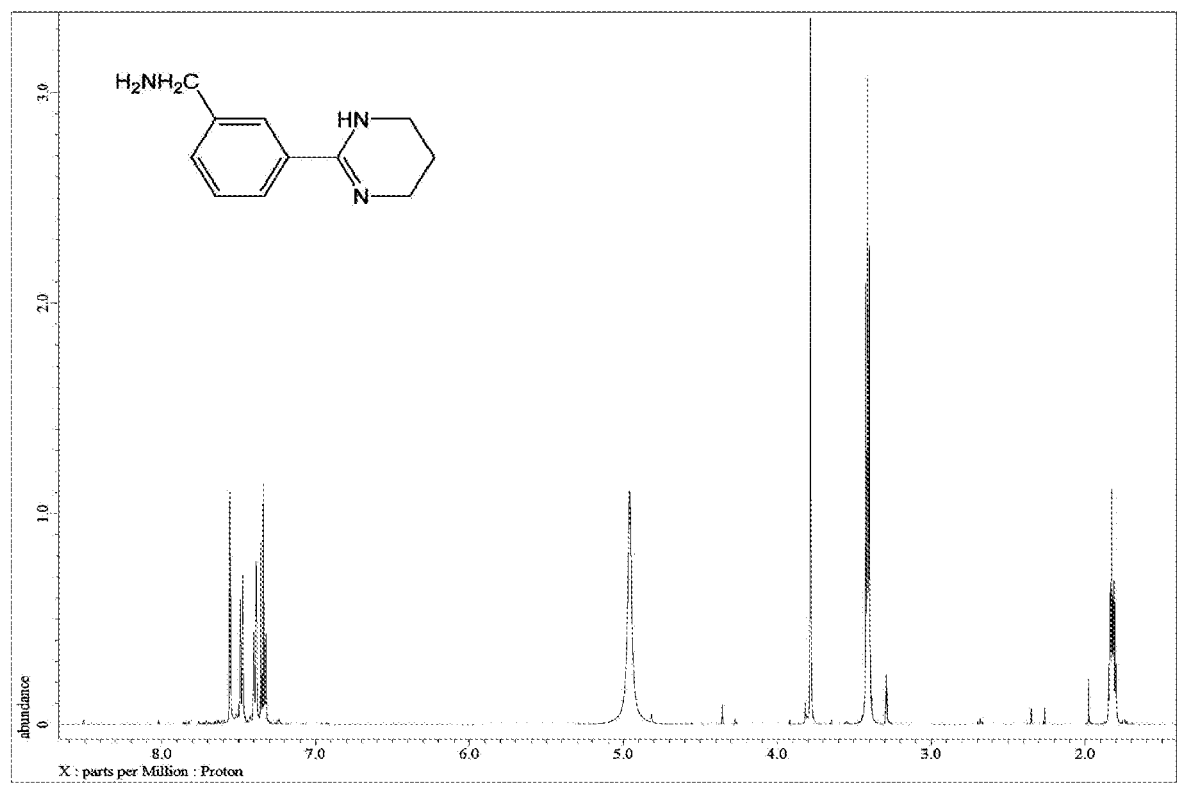
FIG. 5 is a $^1$H-NMR chart of m-aminomethyl phenyl tetrahydropyrimidine.
Figure 6:
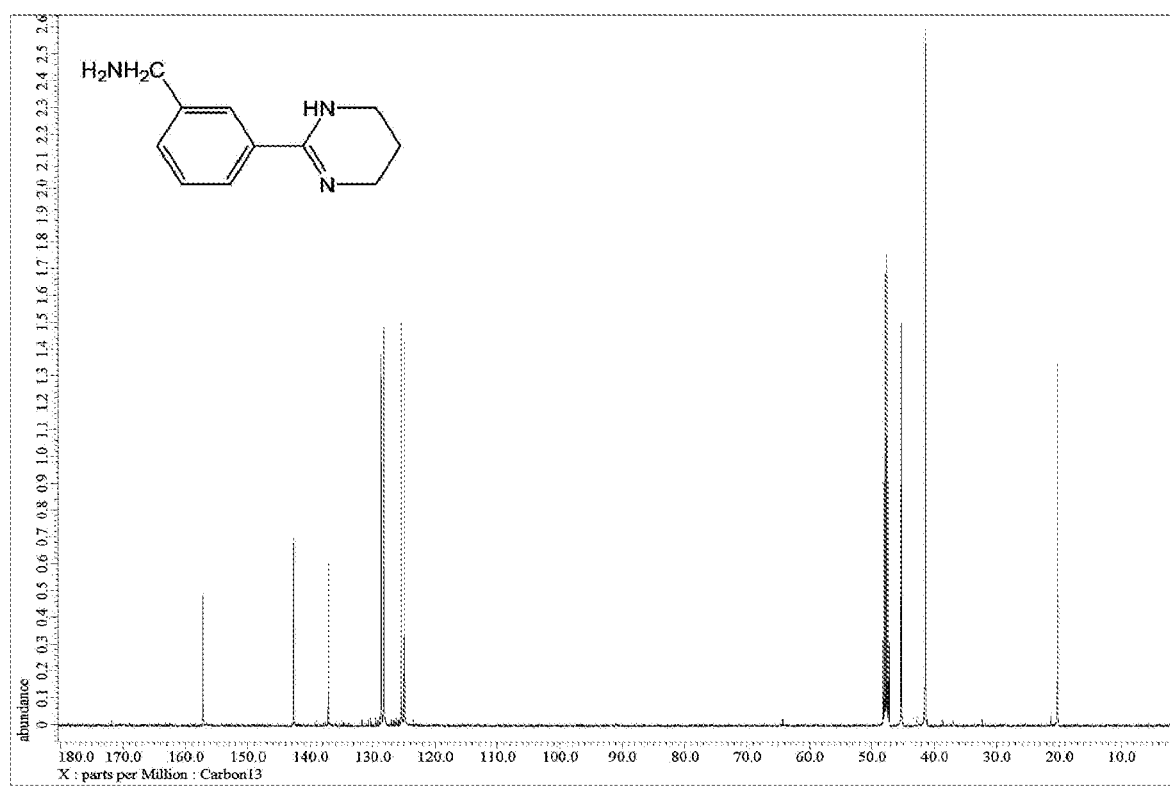
FIG. 6 is a $^{13}$C-NMR chart of m-aminomethyl phenyl tetrahydropyrimidine.
Figure 7:
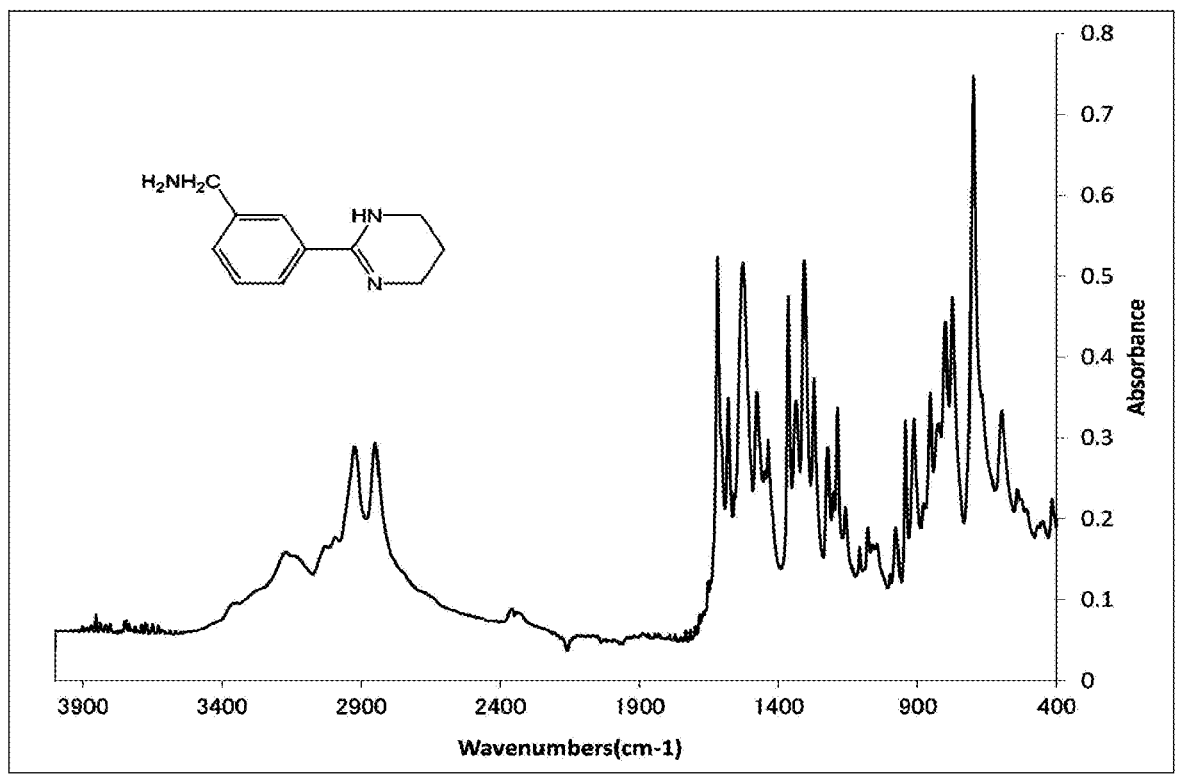
FIG. 7 is an IR chart of m-aminomethyl phenyl tetrahydropyrimidine.
Figure 8:
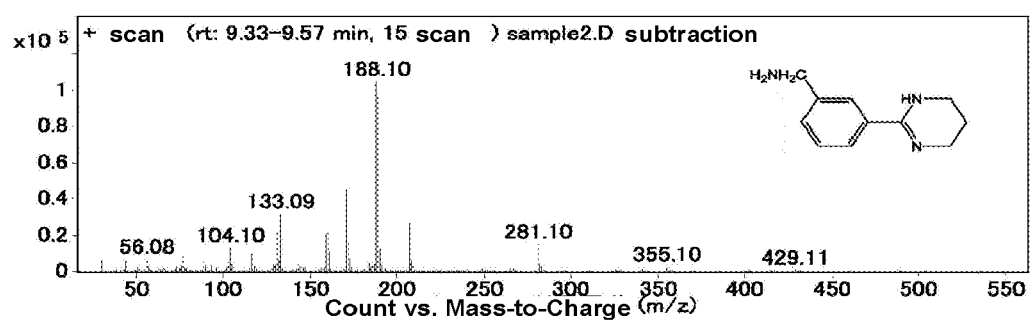
FIG. 8 is a GC-MS EI+ chart of m-aminomethyl phenyl tetrahydropyrimidine.

3-Cyanobenzylamine (5.0 g), 1,3-propanediamine (3.7 g), copper acetate (0.7 g) and meta-xylene (25.0 g) were fed into a 100 mL three-necked flask equipped with a thermometer sleeve and a reflux condenser, and heated for reflux at 134° C. for 4.5 hours while being stirred under atmospheric pressure. After that, the resulting mixture in the flask was left to cool to obtain a solid precipitate, which was then dissolved in tetrahydrofuran. The resulting solution was filtered to separate the catalyst. Further, the solvent was concentrated using an evaporator, followed by simple distillation using a Kugelrohr apparatus, to thereby obtain 1.6 g of a yellow solid. This yellow solid was confirmed as being m-aminomethyl phenyl tetrahydropyrimidine based on the $^1$H- and $^{13}$C-NMR charts (FIGS. 5 and 6), the IR chart (FIG. 7) and the GC-MS El+ chart (FIG. 8). Further, the reaction solution after the separation of the catalyst and insoluble matter by filtration was analyzed by gas chromatography, to find that the yield of the m-aminomethyl phenyl tetrahydropyrimidine was 78%.

In the identification, the following peaks, etc., were found in the NMR and IR charts.

NMR (d4-Methanol): $^1$H δ 7.33-7.57, 4H (benzene ring), 3.77, 2H (—CH$_2$-Ph), 3.41-3.43, 4H (—CH$_2$—(CH$_2$)—CH$_2$— of tetrahydropyrimidine ring), 1.83, 2H (—(CH$_2$)—CH$_2$—(CH$_2$)— of tetrahydropyrimidine ring), $^{13}$C δ 159 (C of tetrahydropyrimidine ring), 126-144 (benzene ring), 46.6 (—CH$_2$—(CH$_2$)—CH$_2$— of tetrahydropyrimidine ring), 42.8 (NH$_2$—CH$_2$-Ph), 21.5 (—(CH$_2$)—CH$_2$—(CH$_2$)— of tetrahydropyrimidine ring) ppm IR (ATR method): ν 3169, 2924, 2849, 1619, 1529, 1365, 1307, 800, 775, 699 cm$^{-1}$ Example 3 m-Aminomethyl Phenyl Imidazoline

Figure 9:
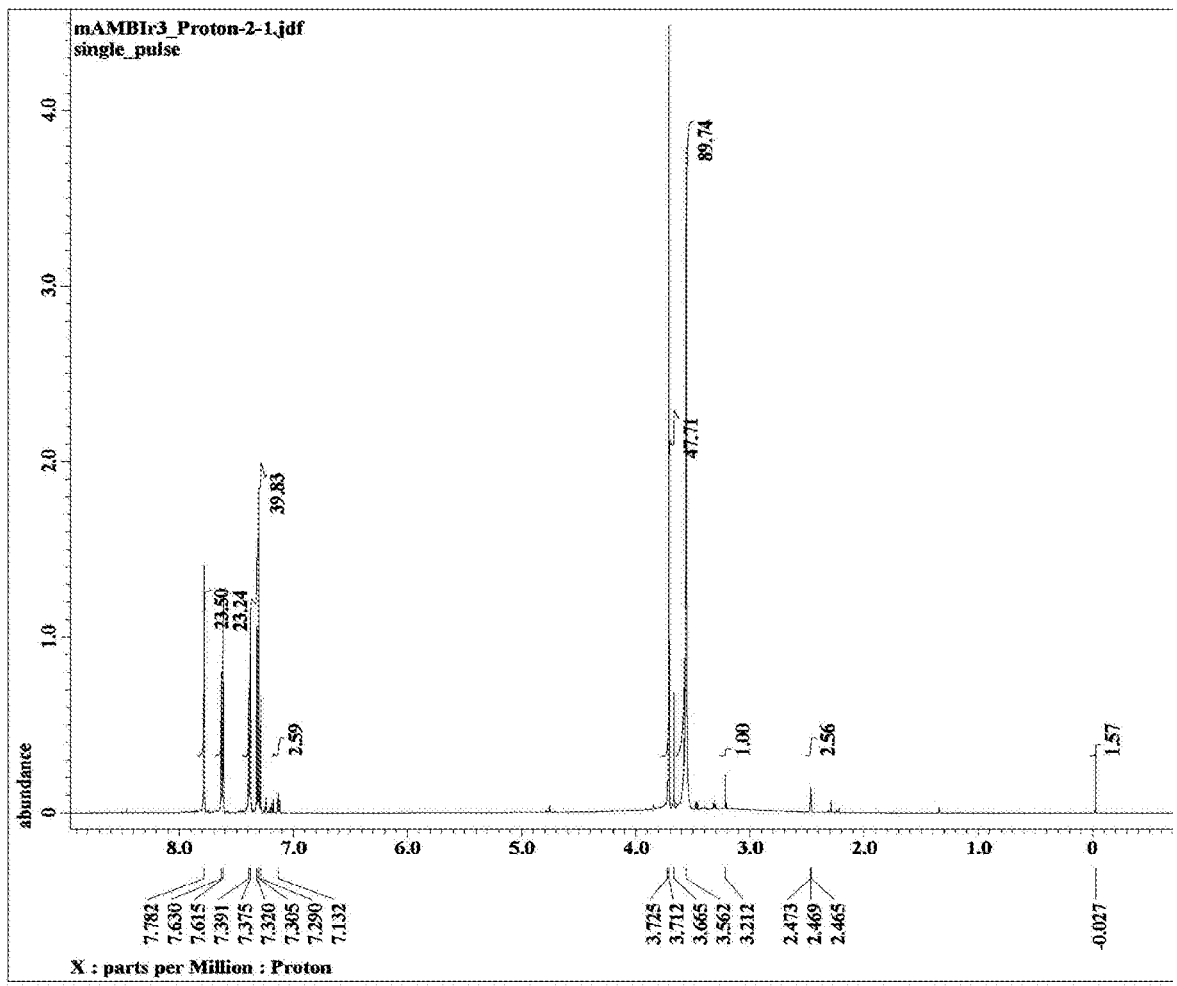
FIG. 9 is a $^1$H-NMR chart of m-aminomethyl phenyl imidazoline.
Figure 10:
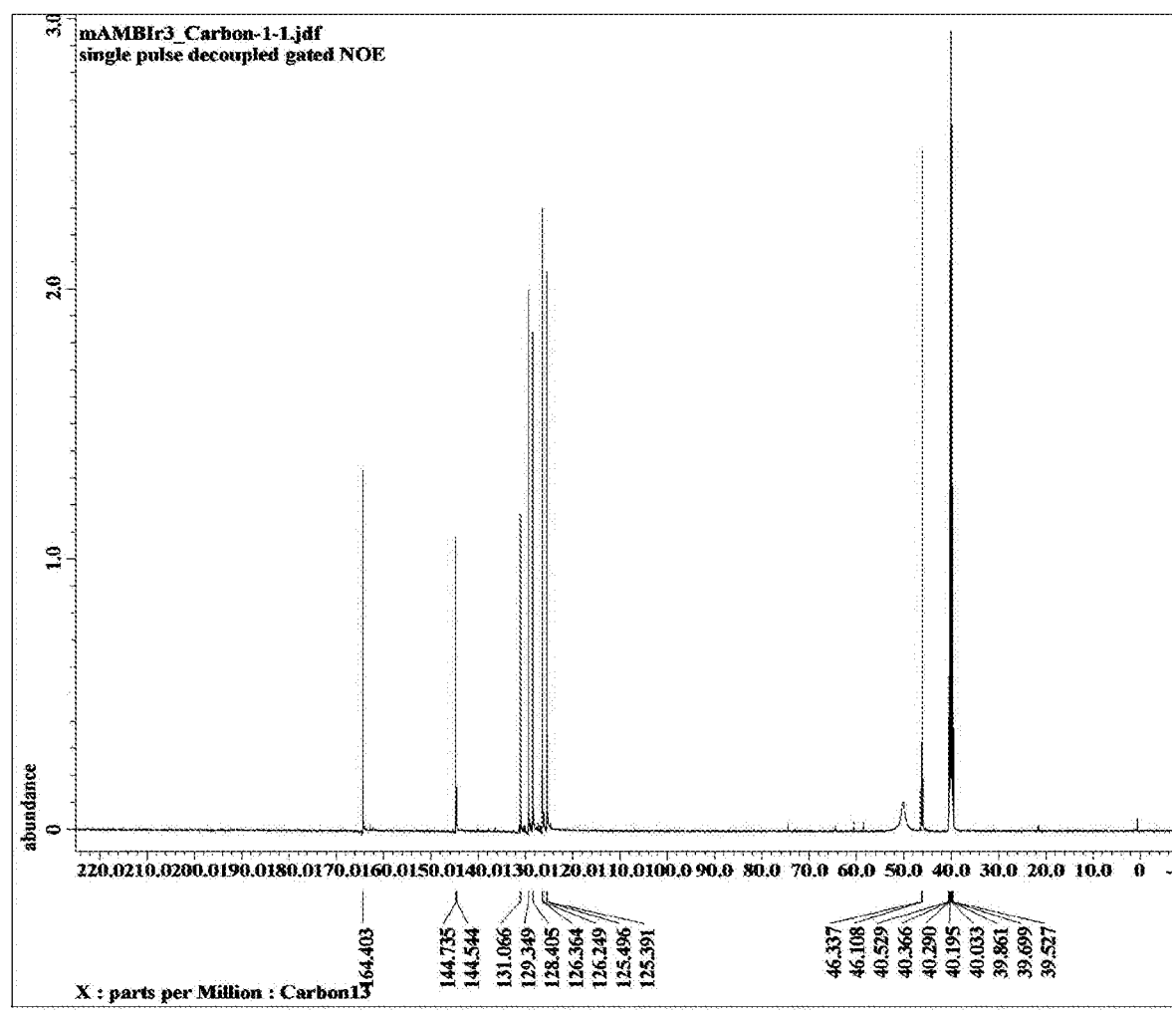
FIG. 10 is a $^{13}$C-NMR chart of m-aminomethyl phenyl imidazoline.
Figure 11:
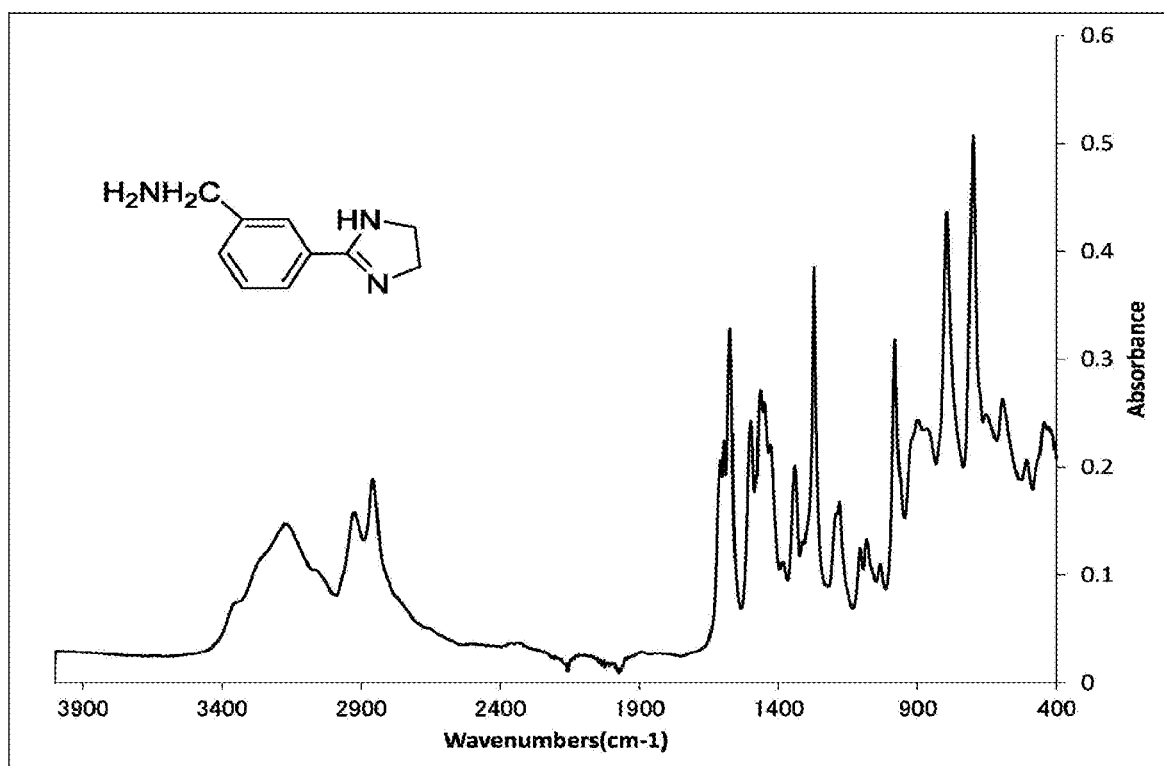
FIG. 11 is an IR chart of m-aminomethyl phenyl imidazoline.
Figure 12:
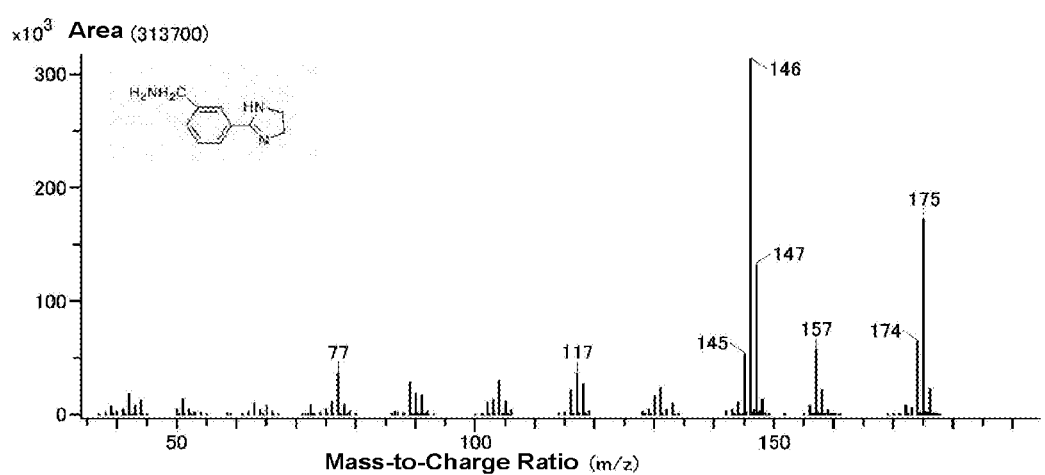
FIG. 12 is a GC-MS EI+ chart of m-aminomethyl phenyl imidazoline.

The m-cyanophenyl imidazoline (3.0 g) obtained in Synthesis Example 2, sodium hydroxide (0.1 g), a commercially available sponge nickel catalyst (0.5 g; R-200 manufactured by Nikko Rica Corporation), and 2-methoxyethanol (30 g) as a solvent were fed into a stainless-steel pressure-resistant container having an internal volume of 100 mL and equipped with a thermometer sleeve and a pressure gauge. After the interior of the reactor was substituted with nitrogen, the reactor was pressurized with hydrogen at 5 MPa and sealed. The container was then heated while being stirred, and held at 50° C. for 1.5 hours. After cooling and pressure falling, the reaction solution was filtered to separate the catalyst. Further, the solvent was concentrated using an evaporator, followed by simple distillation with a Kugelrohr apparatus, to thereby obtain 2.1 g of yellow, transparent liquid. This yellow liquid was confirmed as being m-aminomethyl phenyl imidazoline based on the $^1$H- and $^{13}$C-NMR charts (FIGS. 9 and 10), the IR chart (FIG. 11) and the GC-MS El+ chart (FIG. 12). Further, the reaction solution after the separation of the catalyst and insoluble matter by filtration was analyzed by gas chromatography, to find that the yield of the m-aminomethyl phenyl imidazoline was 80%.

In the identification, the following peaks, etc., were found in the NMR and IR chart.

NMR (d6-DMSO): $^1$H δ 7.29-7.78, 4H (benzene ring), 3.72, 2H (—CH$_2$-Ph), 3.56, 4H (—CH$_2$—CH$_2$— of imidazoline ring), $^{13}$C δ 164 (C of imidazoline ring), 125-144 (benzene ring), 49.5 (—CH$_2$—CH$_2$— of imidazoline ring), 46.1 (NH$_2$—CH$_2$-Ph) ppm IR (ATR method): v 3170, 2924, 2854, 1572, 1464, 1273, 982, 793, 698 cm$^{-1}$ Example 4

3-Methyl-4-Aminomethyl Phenyl Imidazoline

Figure 13:
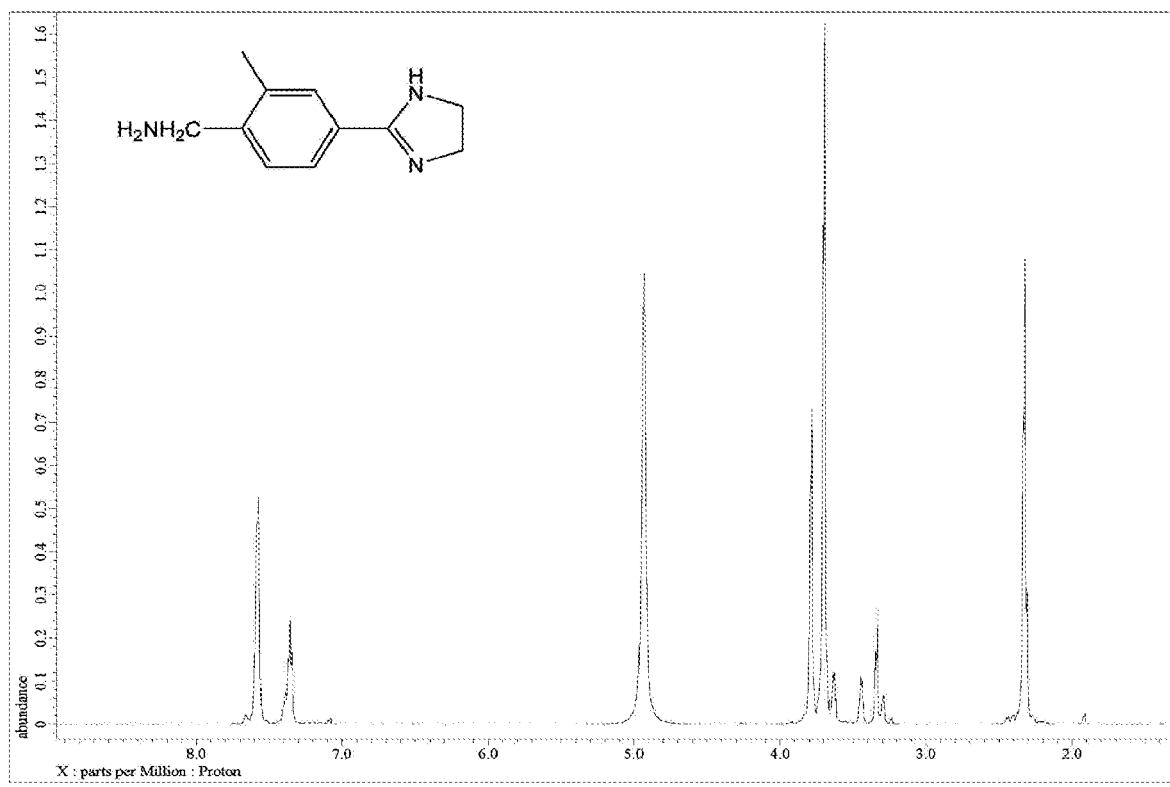
FIG. 13 is a $^1$H-NMR chart of 3-methyl-4-aminomethyl phenyl imidazoline.
Figure 14:
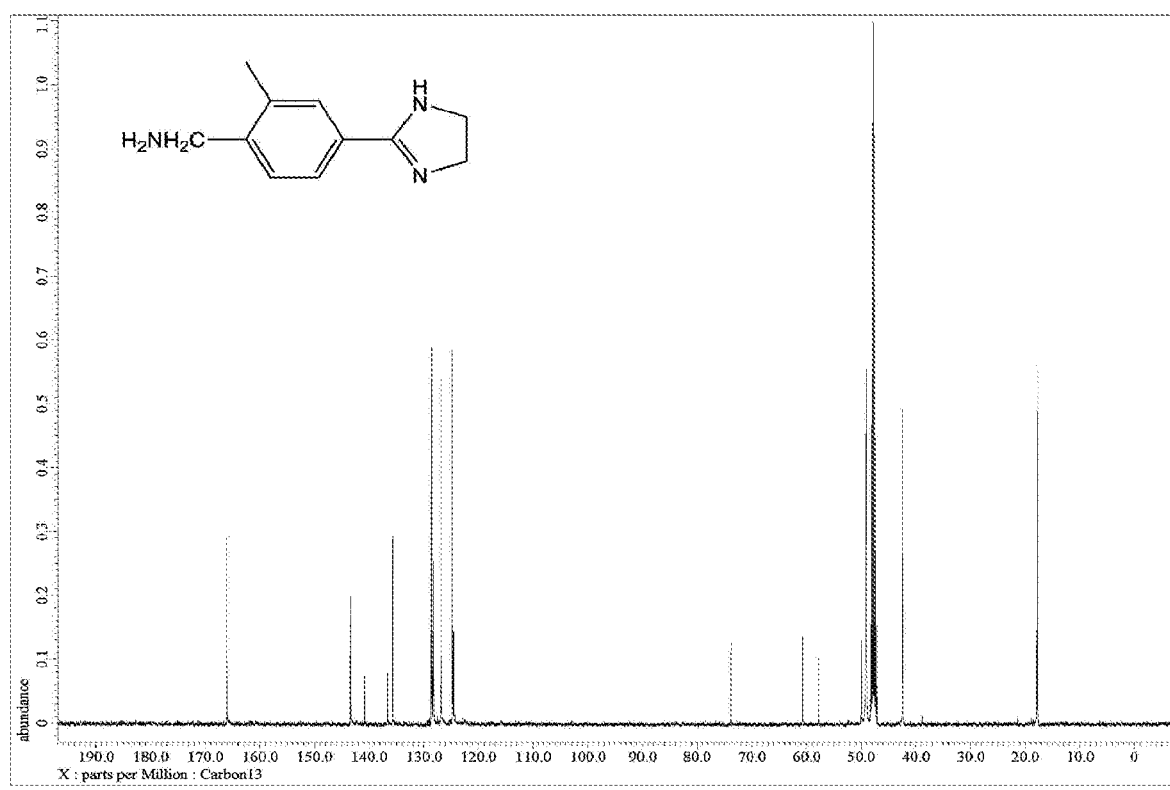
FIG. 14 is a $^{13}$C-NMR chart of 3-methyl-4-aminomethyl phenyl imidazoline.
Figure 15:
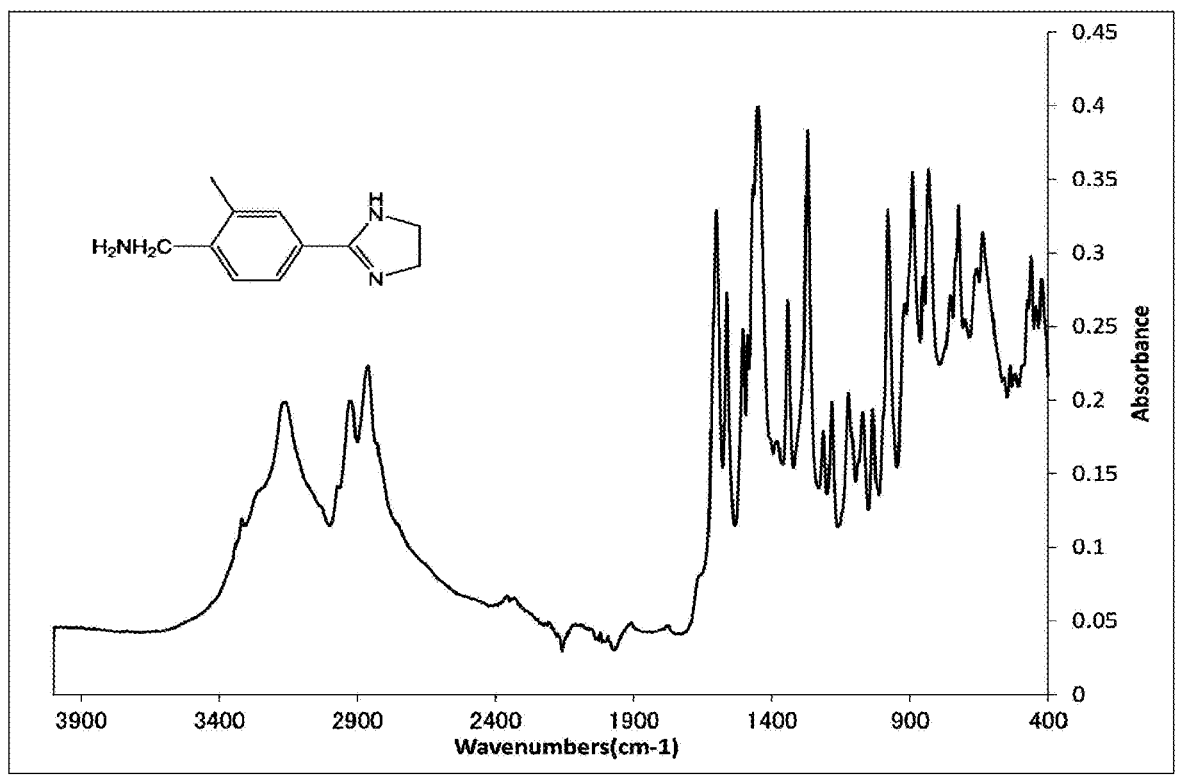
FIG. 15 is an IR chart of 3-methyl-4-aminomethyl phenyl imidazoline.
Figure 16:
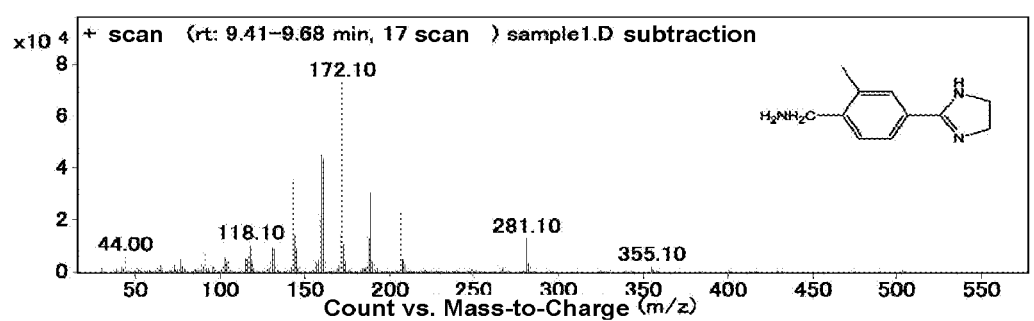
FIG. 16 is a GC-MS EI+ chart of 3-methyl-4-aminomethyl phenyl imidazoline.

The 3-methyl-4-cyanophenyl imidazoline (3.0 g) obtained in Synthesis Example 3, a commercially available sponge nickel catalyst (0.5 g; Raney 6800 manufactured by W.R. Grace and Company), and 2-methoxyethanol (50.0 g) as a solvent were fed into a stainless-steel pressure-resistant container having an internal volume of 200 mL and equipped with a thermometer sleeve and a pressure gauge. After the interior of the reactor was substituted with nitrogen, the reactor was pressurized with hydrogen to 5 MPa and sealed. The container was then heated while being stirred and held at 50-70° C. for 5.4 hours. After cooling and pressure falling, the reaction solution was filtered to separate the catalyst and insoluble matter. Further, the solvent was concentrated using an evaporator, to thereby obtain yellow liquid. This yellow liquid was confirmed as being 3-methyl-4-aminomethyl phenyl imidazoline based on the $^1$H- and $^{13}$C-NMR charts (FIGS. 13 and 14), the IR chart (FIG. 15) and the GC-MS El+ chart (FIG. 16). Further, the reaction solution after the separation of the catalyst and insoluble matter by filtration was analyzed by gas chromatography, to find that the yield of the 3-methyl-4-aminomethyl phenyl imidazoline was 76%.

In the identification, the following peaks, etc., were found in the NMR and IR charts.

IR (ATR method): v 3163, 2927, 2862, 1601, 1450, 1271, 980, 981, 833, 724 cm$^{-1}$ NMR (d4-Methanol): $^1$H δ 7.30-7.54, 3H (benzene ring), 3.75, 2H (—CH$_2$-Ph), 3.66, 4H (—CH$_2$—CH$_2$— of imidazoline ring), 2.29, 3H (methyl of benzene ring), $^{13}$C δ 167(C of imidazoline ring), 126-145 (benzene ring), 50.4 (—CH$_2$—CH$_2$— of imidazoline ring), 43.8 (NH$_2$—CH$_2$-Ph),18.9 (methyl of benzene ring) ppm Example 5

The p-aminomethyl phenyl imidazoline (0.11 g) obtained in Example 1 was added to an epoxy resin (0.32 g; JER828 manufactured by Mitsubishi Chemical Corporation), and stirred for mixing. The obtained mixture was then held in a constant temperature bath at 23° C. and 50% humidity for 24 hours for curing, to thereby obtain a light yellow, transparent, semi-cured resin. The obtained semi-cured resin was completely cured through DSC (temperature increase rate: 10° C./min; measurement temperature: 50-300° C.; nitrogen atmosphere). The resulting resin was again analyzed by DSC under the same conditions to determine a glass transition temperature, which was found to be 98° C. The result is shown in Table 1 below. This result shows that the compound represented by the above-described formula (1) according to the present invention, or a salt thereof, is useful as an epoxy resin curing agent.

Example 6

The m-aminomethyl phenyl tetrahydropyrimidine (0.11 g) obtained in Example 2 was added to an epoxy resin (0.31 g; JER828 manufactured by Mitsubishi Chemical Corporation), and stirred for mixing. The resulting mixture was then held in a constant temperature bath at 23° C. and 50% humidity for 24 hours for curing, to thereby obtain a yellow, transparent semi-cured resin. The obtained semi-cured resin was completely cured through DSC (temperature increase rate: 10° C./min; measurement temperature: 50-300° C.; nitrogen atmosphere). The resulting resin was again analyzed by DSC under the same conditions to determine a glass transition temperature, which was found to be 94° C. The result is shown in Table 1 below. This result shows that the compound represented by the above-described formula (1) according to the present invention, or a salt thereof, is useful as an epoxy resin curing agent.

Example 7

The m-aminomethyl phenyl imidazoline (1.15 g) obtained in Example 3 was added to an epoxy resin (3.7 g; JER828 manufactured by Mitsubishi Chemical Corporation), and stirred for mixing. The resulting mixture was then held in a constant temperature bath at 23° C. and 50% humidity for 24 hours for curing, to thereby obtain a light yellow, transparent semi-cured resin. The obtained semi-cured resin was completely cured through DSC (temperature increase rate: 10° C./min; measurement temperature: 50-300° C.; nitrogen atmosphere). The resulting resin was again analyzed by DSC under the same conditions to determine a glass transition temperature, which was found to be 120° C. The result is shown in Table 1 below. This result shows that the compound represented by the above-described formula (1) according to the present invention, or a salt thereof, is useful as an epoxy resin curing agent.

The obtained epoxy resin compositions were evaluated concerning the drying of coating according to the method set out below. The epoxy resin after stirring and mixing was applied to a glass plate (25 mm×300 mm×2 mm) using a 76 μm applicator, and placed under the conditions of 23° C. and 50% RH so as to measure the coating for both dry-to-touch (i.e., the time until a needle mark was created on the coating) and half-dry (i.e., the time until no needle mark was made on the underlying glass plate) using an RC-type coating drying time measurement device (manufactured by TP GIKEN). The results of this coating drying test were one hour and 24 minutes for the dry-to-touch time and 9 hours and 30 minutes for the half-dry time.

Example 8

The 3-methyl-4-aminomethyl phenyl imidazoline (0.12 g) obtained in Example 4 was added to an epoxy resin (0.36 g; JER828 manufactured by Mitsubishi Chemical Corporation), and stirred for mixing. The resulting mixture was then held in a constant temperature bath at 23° C. and 50% humidity for 24 hours for curing, to thereby obtain a yellow, transparent semi-cured resin. The obtained semi-cured resin was completely cured through DSC (temperature increase rate: 10° C./min; measurement temperature: 50-300° C.; nitrogen atmosphere). The resulting resin was again analyzed by DSC under the same conditions to determine a glass transition temperature, which was found to be 115° C. The result is shown in Table 1 below. This result shows that the compound represented by the above-described formula (1) according to the present invention, or a salt thereof, is useful as an epoxy resin curing agent.

TABLE 1

| Example | Example Number of Raw Material | Raw Material Amine | Glass Transition Temperature |
|---|---|---|---|
| 5 | 1 | p-Aminomethyl phenyl imidazoline | 98° C. |
| 6 | 2 | m-Aminomethyl phenyl tetrahydropyrimidine | 94° C. |
| 7 | 3 | m-Aminomethyl phenyl imidazoline | 120° C. |
| 8 | 4 | 3-Methyl-4-aminomethyl phenyl imidazoline | 115° C. |

Comparative Example 1

2-Phenyl imidazoline (1.02 g; manufactured by Wako Pure Chemical Industries, Ltd.) was added to an epoxy resin (1.28 g; JER828 manufactured by Mitsubishi Chemical Corporation), and stirred for mixing. The resulting mixture was then held in a constant temperature bath at 23° C. and 50% humidity for 24 hours. After that, the surface of the mixture was pressed with a medicine spoon and found to be sticky and to have deformation. The surface of the semi-cured resin obtained in each of Examples 5 to 8 was similarly pressed with a medicine spoon, but no deformation or stickiness was observed. It was accordingly confirmed that the mixture was not cured under the above conditions of Comparative Example 1. This result also shows that the compound represented by the above-described formula (1) according to the present invention or a salt thereof is useful as an epoxy resin curing agent.

From the Examples described above, a novel compound according to the present invention, i.e., a compound represented by the above formula (1), or a salt thereof, has been confirmed to be usable as an epoxy resin curing agent. Accordingly, the present invention is important in the production of thermosetting resins and compositions of such resins, and is therefore of considerable significance.

INDUSTRIAL APPLICABILITY

The compound represented by the above formula (1) according to the present invention or a salt thereof is industrially applicable as raw materials, additives, pharmaceutical intermediates, epoxy resin curing agents, coating agents, adhesive agents and the like. The present application is based on Japanese Patent Application No. JP2017-071059, filed on Mar. 31, 2017, the content of which is incorporated herein.

What is claimed is:

1. A compound represented by formula (1) below, or a salt thereof:

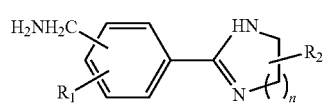

(1)

wherein:
$R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and
n is an integer of 1 or 2,
wherein said compound represented by formula (1) or a salt thereof is not any of the following compounds:
p-aminomethyl phenyl imidazoline represented by formula (2) below or a salt thereof:

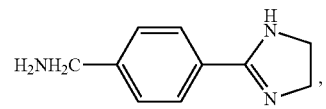

(2)

p-aminomethyl phenyl tetrahydropyrimidine,
m-aminomethyl phenyl tetrahydropyrimidine represented by formula (3) below or a salt thereof:

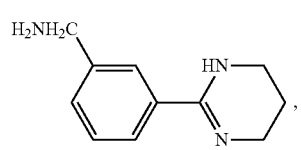

(3)

and
benzenemethanamine, 2-fluoro-4-(1, 4, 5, 6-tetrahydro-2-pyrimidinyl).

2. The compound according to claim 1 or a salt thereof, wherein the compound represented by formula (1) or a salt thereof is:
m-aminomethyl phenyl imidazoline represented by formula (4) below or a salt thereof:

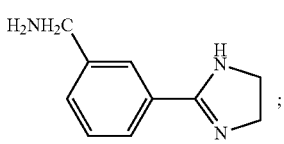

(4)

or
3-methyl-4-aminomethyl phenyl imidazoline represented by formula (5) below or a salt thereof:

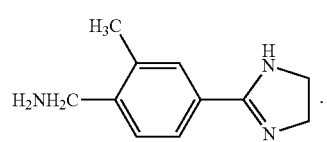

(5)

3. An epoxy resin curing agent, comprising a compound according to claim 1, or a salt thereof.

4. An epoxy resin composition, comprising:
an epoxy resin; and
an epoxy resin curing agent according to claim 3.

5. A method for producing a compound represented by formula (1) or a salt thereof, the method comprising reacting a cyanobenzylamine compound represented by formula (6) or a salt thereof with an ethylenediamine compound represented by formula (7) or a salt thereof, or with a propanediamine compound represented by formula (7) or a salt thereof, to obtain a compound represented by formula (1) or a salt thereof:

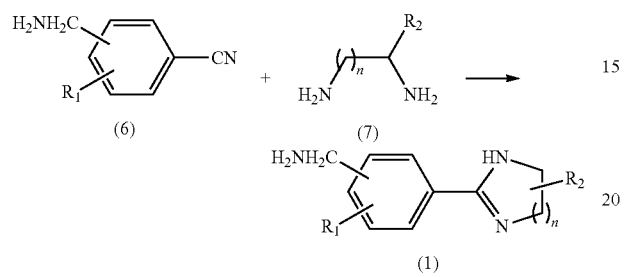

wherein, in formula (1), formula (6) and formula (7):
$R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and
n is an integer of 1 or 2,
wherein said compound represented by formula (1) or a salt thereof is not any of the following compounds:
p-aminomethyl phenyl imidazoline represented by formula (2) below or a salt thereof:

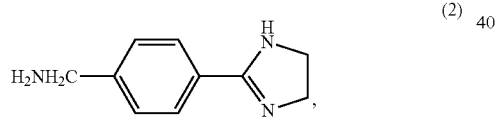

p-aminomethyl phenyl tetrahydropyrimidine, and
m-aminomethyl phenyl tetrahydropyrimidine represented by formula (3) below or a salt thereof:

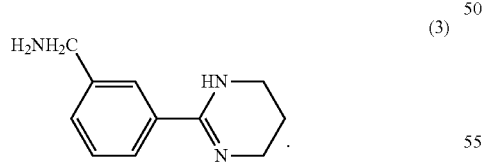

6. A method for producing a compound represented by formula (1) or a salt thereof, the method comprising reducing, with hydrogen, a cyanophenyl imidazoline compound represented by formula (8) or a salt thereof, or a cyanophenyl tetrahydropyrimidine compound represented by formula (8) or a salt thereof, in the presence of a catalyst and a solvent, to obtain a compound represented by formula (1) or a salt thereof:

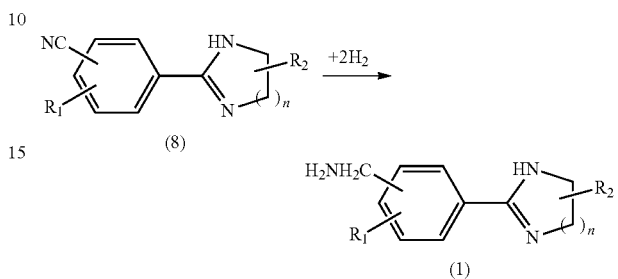

wherein, in formula (1) and formula (8):
$R_1$ and $R_2$ each independently represent hydrogen or a substituent selected from the group consisting of an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and
n is an integer of 1 or 2,
wherein said compound represented by formula (1) or a salt thereof is not any of the following compounds:
p-aminomethyl phenyl imidazoline represented by formula (2) below or a salt thereof:

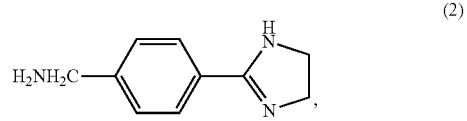

p-aminomethyl phenyl tetrahydropyrimidine, and
m-aminomethyl phenyl tetrahydropyrimidine represented by formula (3) below or a salt thereof:

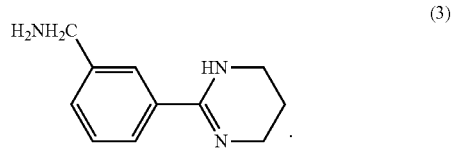

\* \* \* \* \*